(12) United States Patent
Singh et al.

(10) Patent No.: US 8,002,313 B2
(45) Date of Patent: Aug. 23, 2011

(54) INLINE SWIVEL CONNECTION FOR MULTI-LUMEN TUBING

(75) Inventors: Vinay K. Singh, San Antonio, TX (US); Larry D. Swain, San Antonio, TX (US); Douglas A. Cornet, San Antonio, TX (US); Robert Peyton Wilkes, San Antonio, TX (US); Keith Patrick Heaton, Poole (GB); Christopher Brian Locke, Bournemouth (GB); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 1085 days.

(21) Appl. No.: 11/789,719

(22) Filed: Apr. 24, 2007

(65) Prior Publication Data
US 2008/0011368 A1    Jan. 17, 2008

Related U.S. Application Data

(60) Provisional application No. 60/794,724, filed on Apr. 25, 2006.

(51) Int. Cl.
*F16L 27/00* (2006.01)

(52) U.S. Cl. .............. 285/123.15; 285/121.3; 285/124.2; 285/124.4; 285/904

(58) Field of Classification Search ............... 285/121.1, 285/121.3, 276, 121.6, 124.1, 144.1, 148.4, 285/148.1, 124.2, 124.3, 124.4, 124.5, 242, 285/371, 398, 136.1, 904, 123.15
See application file for complete search history.

(56) References Cited

U.S. PATENT DOCUMENTS 182,435 A * 9/1876 Guyer
(Continued)

FOREIGN PATENT DOCUMENTS

AU         550575 A1    8/1982
(Continued)

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).

(Continued)

*Primary Examiner* — James M Hewitt
*Assistant Examiner* — Jay R Ripley
(74) *Attorney, Agent, or Firm* — SNR Denton US LLP

(57) ABSTRACT

An apparatus for connecting multi-lumen conduits may include a conduit adapter and a conduit collar. The conduit adapter may include a housing, a bayonet connector, and a support member connecting the housing and the bayonet connector. The support member has an aperture that permits fluid communication through the support member. One end of the conduit collar is sized for insertion into the housing, and a second end is adapted to receive a first multi-lumen conduit. The housing also is adapted to receive a second multi-lumen conduit. The bayonet connector engages a primary lumen of the first multi-lumen conduit and the second multi-lumen conduit such that the primary lumen of the second multi-lumen conduit fluidly communicates with the primary lumen of the first multi-lumen conduit. The conduit adapter and the conduit collar are capable of 360 degree rotation relative to each other about a common axis.

1 Claim, 8 Drawing Sheets

U.S. PATENT DOCUMENTS

| | | | |
|---|---|---|---|
| 320,635 A | * | 6/1885 | Daudt |
| 724,675 A | * | 4/1903 | Decker .................. 285/124.1 |
| 951,516 A | * | 3/1910 | Stephens .................. 285/276 |
| 1,355,846 A | | 10/1920 | Rannells |
| 2,148,566 A | * | 2/1939 | Leon ...................... 285/148.4 |
| 2,213,043 A | * | 8/1940 | Jacobsson et al. ......... 285/276 |
| 2,547,758 A | | 4/1951 | Keeling |
| 2,632,443 A | | 3/1953 | Lesher |
| 2,682,873 A | | 7/1954 | Evans et al. |
| 2,910,763 A | | 11/1959 | Lauterbach |
| 2,969,057 A | | 1/1961 | Simmons |
| 3,066,672 A | | 12/1962 | Crosby, Jr. et al. |
| 3,367,332 A | | 2/1968 | Grover |
| 3,446,245 A | * | 5/1969 | Snyder, Jr. ................. 285/276 |
| 3,503,634 A | * | 3/1970 | Cadiou .................. 285/124.3 |
| 3,512,540 A | * | 5/1970 | Hughes .................. 285/276 |
| 3,520,300 A | | 7/1970 | Flower, Jr. |
| 3,568,675 A | | 3/1971 | Harvey |
| 3,648,692 A | | 3/1972 | Wheeler |
| 3,682,180 A | | 8/1972 | McFarlane |
| 3,731,705 A | * | 5/1973 | Butler |
| 3,826,254 A | | 7/1974 | Mellor |
| 3,889,983 A | * | 6/1975 | Freize et al. .............. 285/276 |
| 4,080,970 A | | 3/1978 | Miller |
| 4,096,853 A | | 6/1978 | Weigand |
| 4,139,004 A | | 2/1979 | Gonzalez, Jr. |
| 4,165,748 A | | 8/1979 | Johnson |
| 4,184,510 A | | 1/1980 | Murry et al. |
| 4,233,969 A | | 11/1980 | Lock et al. |
| 4,245,630 A | | 1/1981 | Lloyd et al. |
| 4,256,109 A | | 3/1981 | Nichols |
| 4,261,363 A | | 4/1981 | Russo |
| 4,275,721 A | | 6/1981 | Olson |
| 4,284,079 A | | 8/1981 | Adair |
| 4,297,995 A | | 11/1981 | Golub |
| 4,333,468 A | | 6/1982 | Geist |
| 4,373,519 A | | 2/1983 | Errede et al. |
| 4,382,441 A | | 5/1983 | Svedman |
| 4,392,853 A | | 7/1983 | Muto |
| 4,392,858 A | | 7/1983 | George et al. |
| 4,419,097 A | | 12/1983 | Rowland |
| 4,462,617 A | * | 7/1984 | Green ..................... 285/276 |
| 4,465,485 A | | 8/1984 | Kashmer et al. |
| 4,475,909 A | | 10/1984 | Eisenberg |
| 4,480,638 A | | 11/1984 | Schmid |
| 4,525,166 A | | 6/1985 | Leclerc |
| 4,525,374 A | | 6/1985 | Vaillancourt |
| 4,540,412 A | | 9/1985 | Van Overloop |
| 4,543,100 A | | 9/1985 | Brodsky |
| 4,548,202 A | | 10/1985 | Duncan |
| 4,551,139 A | | 11/1985 | Plaas et al. |
| 4,569,348 A | | 2/1986 | Hasslinger |
| 4,605,399 A | | 8/1986 | Weston et al. |
| 4,608,041 A | | 8/1986 | Nielsen |
| 4,640,688 A | | 2/1987 | Hauser |
| 4,655,754 A | | 4/1987 | Richmond et al. |
| 4,664,662 A | | 5/1987 | Webster |
| 4,688,831 A | * | 8/1987 | Viehmann ................. 285/124.4 |
| 4,710,165 A | | 12/1987 | McNeil et al. |
| 4,732,414 A | * | 3/1988 | Inaba |
| 4,733,659 A | | 3/1988 | Edenbaum et al. |
| 4,743,232 A | | 5/1988 | Kruger |
| 4,754,782 A | * | 7/1988 | Grantham |
| 4,758,220 A | | 7/1988 | Sundblom et al. |
| 4,787,888 A | | 11/1988 | Fox |
| 4,826,494 A | | 5/1989 | Richmond et al. |
| 4,838,883 A | | 6/1989 | Matsuura |
| 4,840,187 A | | 6/1989 | Brazier |
| 4,863,449 A | | 9/1989 | Therriault et al. |
| 4,865,354 A | * | 9/1989 | Allen ..................... 285/124.1 |
| 4,872,450 A | | 10/1989 | Austad |
| 4,878,901 A | | 11/1989 | Sachse |
| 4,897,081 A | | 1/1990 | Poirier et al. |
| 4,906,233 A | | 3/1990 | Moriuchi et al. |
| 4,906,240 A | | 3/1990 | Reed et al. |
| 4,919,654 A | | 4/1990 | Kalt et al. |
| 4,941,882 A | | 7/1990 | Ward et al. |
| 4,953,565 A | | 9/1990 | Tachibana et al. |
| 4,969,880 A | | 11/1990 | Zamierowski |
| 4,985,019 A | | 1/1991 | Michelson |
| 5,037,397 A | | 8/1991 | Kalt et al. |
| 5,086,170 A | | 2/1992 | Luheshi et al. |
| 5,092,858 A | | 3/1992 | Benson et al. |
| 5,100,396 A | | 3/1992 | Zamierowski |
| 5,134,994 A | | 8/1992 | Say |
| 5,149,331 A | | 9/1992 | Ferdman et al. |
| 5,167,613 A | | 12/1992 | Karami et al. |
| 5,176,663 A | | 1/1993 | Svedman et al. |
| 5,215,522 A | | 6/1993 | Page et al. |
| 5,232,453 A | | 8/1993 | Plass et al. |
| 5,261,893 A | | 11/1993 | Zamierowski |
| 5,278,100 A | | 1/1994 | Doan et al. |
| 5,279,550 A | | 1/1994 | Habib et al. |
| 5,285,744 A | * | 2/1994 | Grantham et al. |
| 5,298,015 A | | 3/1994 | Komatsuzaki et al. |
| 5,342,376 A | | 8/1994 | Ruff |
| 5,344,415 A | | 9/1994 | DeBusk et al. |
| 5,358,494 A | | 10/1994 | Svedman |
| 5,437,622 A | | 8/1995 | Carion |
| 5,437,651 A | | 8/1995 | Todd et al. |
| 5,527,293 A | | 6/1996 | Zamierowski |
| 5,549,584 A | | 8/1996 | Gross |
| 5,556,375 A | | 9/1996 | Ewall |
| 5,607,388 A | | 3/1997 | Ewall |
| 5,636,643 A | | 6/1997 | Argenta et al. |
| 5,645,081 A | | 7/1997 | Argenta et al. |
| 5,913,336 A | * | 6/1999 | Ingram ...................... 285/124.2 |
| 6,071,267 A | | 6/2000 | Zamierowski |
| 6,135,116 A | | 10/2000 | Vogel et al. |
| 6,196,596 B1 | * | 3/2001 | Kwok et al. ............. 285/123.15 |
| 6,241,747 B1 | | 6/2001 | Ruff |
| 6,287,316 B1 | | 9/2001 | Agarwal et al. |
| 6,345,623 B1 | | 2/2002 | Heaton et al. |
| 6,488,643 B1 | | 12/2002 | Tumey et al. |
| 6,493,568 B1 | | 12/2002 | Bell et al. |
| 6,553,998 B2 | | 4/2003 | Heaton et al. |
| 6,814,079 B2 | | 11/2004 | Heaton et al. |
| 7,399,001 B2 | * | 7/2008 | Maier ....................... 285/121.1 |
| 2002/0077661 A1 | | 6/2002 | Saadat |
| 2002/0115951 A1 | | 8/2002 | Norstrem et al. |
| 2002/0120185 A1 | | 8/2002 | Johnson |
| 2002/0143286 A1 | | 10/2002 | Tumey |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |

OTHER PUBLICATIONS

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Đukić, Ž. Maksimović, Đ. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastman, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, May 2, 1986, pp. 42-46, and 7 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

* cited by examiner

US 8,002,313 B2

INLINE SWIVEL CONNECTION FOR MULTI-LUMEN TUBING

CROSS-REFERENCE TO RELATED APPLICATIONS

This application claims the benefit of and priority to U.S. Provisional Application No. 60/794,724 filed Apr. 25, 2006, which is hereby incorporated by reference.

BACKGROUND OF THE INVENTION

1. Field of the Invention

The invention relates generally to methods and devices for conducting fluids and gases within a reduced pressure treatment system. The invention relates more specifically to an inline connector for multi-lumen tubing that allows free rotation of one end of the tubing with respect to the other end of the tubing.

2. Description of Related Art

General Background of Tissue Treatment

Various therapies have been developed over time to facilitate the process of tissue growth and healing. Wound closure is one application of tissue growth and healing. Wound closure generally involves the inward migration of epithelial and subcutaneous tissue adjacent the wound. This migration is ordinarily assisted by the inflammatory process, whereby blood flow is increased and various functional cell types are activated. As a result of the inflammatory process, blood flow through damaged or broken vessels is stopped by capillary level occlusion, whereafter cleanup and rebuilding operations may begin. Unfortunately, this process is hampered when a wound is large or has become infected. In such wounds, a zone of stasis (i.e. an area in which localized swelling of tissue restricts the flow of blood to the tissues) forms near the surface of the wound.

Without sufficient blood flow, the epithelial and subcutaneous tissues surrounding the wound not only receive diminished oxygen and nutrients, but are also less able to successfully fight bacterial infection and, thus, less able to naturally close the wound and heal the tissue. Additionally, some wounds harden and inflame to such a degree that closure by stapling or suturing is not feasible. Examples of wounds not readily treatable with staples or suturing include large, deep, open wounds; decubitus ulcers; ulcers resulting from chronic osteomyelitis; and partial thickness burns that subsequently develop into full thickness burns.

As a result of the shortcomings of mechanical wound closure devices, methods and apparatuses for draining wounds by applying continuous and/or periodic reduced pressures have been developed. When applied over a sufficient area of the wound, such reduced pressures have been found to promote the migration of epithelial and subcutaneous tissues toward the wound. In practice, the application of reduced pressure to a wound typically involves the mechanical-like contraction of the wound with simultaneous removal of excess fluid. In this manner, reduced pressure treatment augments the body's natural inflammatory process while alleviating many of the known intrinsic side effects, such as the production of edema caused by increased blood flow absent the necessary vascular structure for proper venous return.

One important component of a reduced pressure treatment system is the conduit system that connects the reduced pressure source (a vacuum pump, typically) to the tissue contact components (a granular foam layer or other manifolding device, typically) enclosed within a pad or wound dressing. This reduced pressure conduit structure may include a more complex multi-lumen structure in order to provide ancillary conduits for monitoring and alternative treatment regimens. The ability to maintain a clear, consistent, and leak-free connection is important within an effective reduced pressure treatment system. Various efforts have been made in the past to provide suitable conduit configurations to effectively connect the reduced pressure source to the tissue treatment site at the wound bed.

Efforts to Maintain Conduit Connection Integrity

A variety of systems and devices are utilized in the veterinary medicine environment to connect animal subjects to medical instrumentation. In both research and treatment situations it is often necessary to connect electrical wires and tubular conduit lines between stationary instrumentation and the subject animal that is typically moving about an enclosure when not sedated. The use of reduced pressure tissue treatment regimens with animal subjects, both for research purposes (i.e. to develop systems intended for human use) and for veterinary systems intended for animal treatment, has become more frequent. Such reduced pressure tissue treatment systems are implemented on a variety of animals, large and small, from mice and rats to rabbits and sheep.

Inherent in reduced pressure tissue treatment systems is the use of a number of tubular conduit lines connecting the tissue site on the subject animal to stationary instrumentation typically in the form of negative pressure sources and the associated fluid containers. With human patients, it is often possible (although certainly not always possible) to insist upon reduced mobility or even immobile conditions in order to carry out the tissue treatment. With animal patients, this is of course generally not possible at all unless the animal is sedated. As the preference is to permit the tissue to heal over a period of time, it is generally not practical to maintain sedation of an animal to carry out either research or treatment with reduced pressure application. The problems that arise therefore in maintaining an effective connection between the negative pressure instrumentation and the reduced pressure treatment dressing can become complex. A direct connection between the instrumentation and the wound dressing can quickly become disabled with the movement of the subject animal even within a relatively small enclosure. Typically the movement includes not just side to side motion, but rotational motion often in the form of walking circles around the enclosure. A direct link therefore with tubing between the instrumentation and the wound site could never be maintained without some rotationally moveable connection.

Efforts have been made in the past to provide swivel or rotational connections between tubing or other liquid/gas conduits between a patient or subject animal and the associated treatment instrumentation. Where the tubing is a single lumen tube, this swivel connection generally need not be complex. However, where multi-lumen tubing is utilized, maintaining the structural simplicity of the connector becomes more challenging. Many reduced pressure tissue treatment systems do utilize multi-lumen tubing to carry out a number of functions between the instrumentation and the wound site. Typically a large primary lumen is used to conduct the reduced pressure to the wound site and thereby draw out fluids and exudates from the wound bed. Ancillary to this larger primary lumen are typically one or more (often four radially spaced) smaller lumens that serve to provide a clear path between the reduced pressure treatment instrumentation and the wound site for the purpose of measuring pressure or carrying out other similar therapeutic functions. It is important for these ancillary lumens to remain clear in order for accurate pressure measurements to be made and the treatment regimen to be carried out accurately. Many efforts have been made to isolate the primary lumen from the ancillay lumens in order to prevent the clogging or contamination of the smaller ancillary lumens with fluids and solids being withdrawn from the wound bed.

Some past efforts have focused on providing movable instrumentation by positioning the reduced pressure treatment equipment on an elevated turntable that freely rotates above the animal enclosure and enjoys a direct connection (without an inline swivel tubing connector) between the instrumentation and the wound dressing. Such efforts clearly suffer, however, from the complexities associated with maintaining a turntable integrating all of the electronic and electrical components necessary to carry out the reduced pressure treatment regimens prescribed. In addition, such systems generally work only for very large animal subjects as even with the best support structures a greater force is required to initiate the rotation of the entire instrument laden turntable.

A number of problems arise in attempting to provide a swivel connector for a multi-lumen tube of the structure described above. Initially, a certain level of complexity is required in order to address the connections between more than a single lumen, even where the ancillary lumens are positioned radially outward from the primary lumen, as is typically the case. The continuity of all lumens must be maintained through the swivel connection. An added concern, however, is the increased risk of cross-contamination between the larger primary lumen and the ancillary smaller lumens that need to remain clear. Any leakage in the swivel connector structure could cause fluids and solids to find their way into the small ancillary lumens, thereby clogging those lines and reducing or preventing the effectiveness of the reduced pressure treatment system.

One further complication that arises as a result of the application of such reduced pressure treatment systems to veterinary environments is the wide range in animal size that the systems must accommodate. In order to prevent cross-contamination or leakage in general from a tubing connector, it is necessary that the connector be sufficiently sealed. Providing a tight seal, however, works contrary to the general requirement of providing an easily rotatable connection. The smaller the subject animal involved, the more easily rotatable the connection must be in order to be effective. Larger animals and most human subjects may of course readily rotate a tighter connection. Smaller animals and small children may be wholly unable to rotate a tight connection, resulting in an ineffective swivel connector.

There is a significant need therefore for a rotating or swivel connector for use in conjunction with multi-lumen conduit of the type typically utilized in reduced pressure tissue treatment systems. It would be desirable if such a connector could accommodate both large and small animals, as well as human subjects, through an adjustment of the connection and therefore the rotational force required to turn the connection. In addition, because such connectors often become points of fluid and solid material deposits, it would be desirable if such a connector could be constructed of inexpensive and therefore disposable material that would not require the connector to be repeatedly cleaned between uses.

BRIEF SUMMARY OF THE INVENTION

The problems presented by existing treatment systems are solved by the systems and methods of the present invention.

In accordance with one embodiment of the present invention, an apparatus for connecting multi-lumen conduits is provided. In such an embodiment, the apparatus comprises a conduit adapter and a conduit collar. The conduit adapter may include a housing, a bayonet connector, and a support member connecting the housing and the bayonet connector. The bayonet connector generally has a single bore extending lengthwise through the connector, and optionally a conduit stop that limits the extent to which the connector may be inserted into a conduit. The support member includes at least one aperture that permits fluid or gas communication through the support member. The conduit collar has a first end and a second end. The first end is sized for insertion into the housing, and the second end is adapted to receive a first multi-lumen conduit. The housing is adapted to receive the first end of the conduit collar such that the bayonet connector engages a primary lumen of the first multi-lumen conduit and the primary lumen of the first multi-lumen conduit fluidly communicates with the bore. The housing also is adapted to receive a second multi-lumen conduit such that the bayonet connector engages a primary lumen of the second multi-lumen conduit, and the primary lumen of the second multi-lumen conduit fluidly communicates with the bore and the primary lumen of the first multi-lumen conduit. The conduit adapter and the conduit collar are capable of 360 degree rotation relative to each other about an axis shared by the conduit adapter and the conduit collar, while permitting fluid communication between ancillary lumens of the first multi-lumen conduit and the second multi-lumen conduit through the aperture in the support member.

In still another embodiment of the present invention, a swivel connector assembly for connecting multi-lumen conduits is provided. In such an embodiment the assembly comprises a connection collar having a first threaded section, a first bulkhead positioned within the connection collar, a conduit adapter, a bearing collar having a second threaded section, a spacer collar, a mounting plate, a shaft, a bearing assembly, and a conduit collar. The conduit adapter comprises a housing, a bayonet connector having a single bore and a conduit stop, a support member connecting the housing and the bayonet connector, and an aperture through the support member. The spacer collar is positioned between the connection collar and the bearing collar, and the mounting plate between the bearing collar and the connection collar. One end of the bearing assembly is coupled to the shaft. The threaded section of the bearing collar is engaged with the threaded section of the connection collar. A first end of the conduit collar is positioned within the adapter and the second end of the conduit collar is positioned within the shaft.

Other objects, features, and advantages of the present invention will become apparent with reference to the drawings and detailed description that follow.

DETAILED DESCRIPTION OF THE PREFERRED EMBODIMENT

In the following detailed description of preferred embodiments, reference is made to the accompanying drawings which form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical mechanical, structural, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

A rotating swivel connector according to one embodiment of the present invention is used in conjunction with multi-lumen conduit, such as the type often used in reduced pressure treatment systems. The connector assembly comprises a conduit adapter and a conduit collar that mate two sections of tubing together in a manner that allows for relatively free rotation. Surrounding the conduit adapter and the conduit collar are larger, threaded enclosure components that control the relative, axial positioning of the conduit adapter and the conduit collar, which serves to maintain a connection and vary the level of force required to rotate the connection. A group of "stationary components" position and hold a conduit that typically extends from the instrumentation used in a reduced pressure treatment system. A second group of components, generally characterized as "rotational components," include a rotational bearing assembly that is attached to a rotating shaft that grips and positions the conduit collar, which is attached to a conduit connected to a subject animal or human patient (at the tissue site). The assembly may be modified to accommodate significant variations in the size of the subject animal or the human patient. The basic components allow the user to vary the tightness of the connection, and therefore the ease with which the connection swivels or rotates, by rotating one threaded enclosure component into or out from a second threaded enclosure component, thereby varying the amount of rotational friction between the conduit adapter and the conduit collar.

Figure 1:
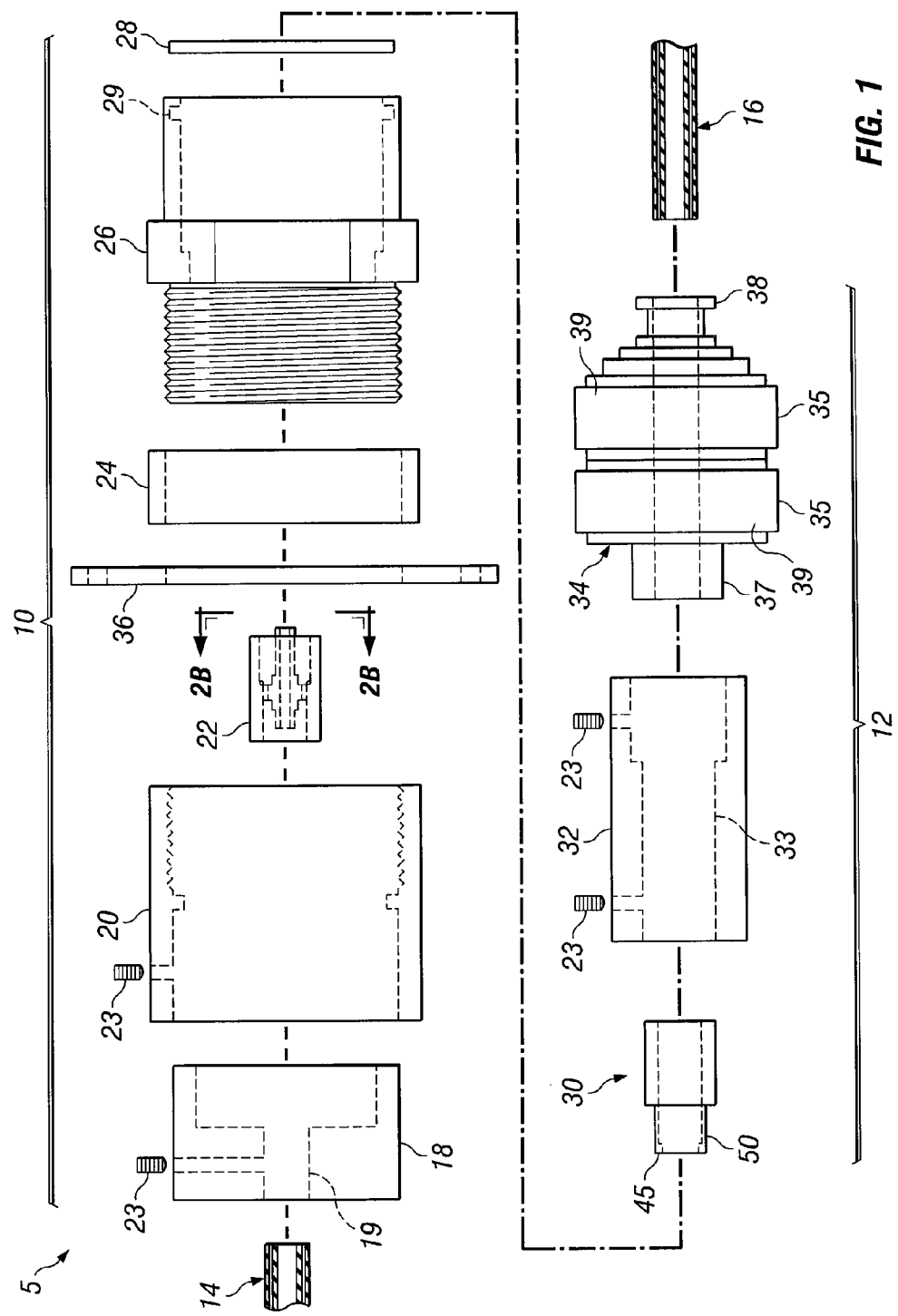
FIG. 1 is an exploded side view having a portion shown with hidden lines of a swivel connector assembly according to an embodiment of the present invention including a conduit connector for receiving two multi-lumen conduits.
Figure 6:
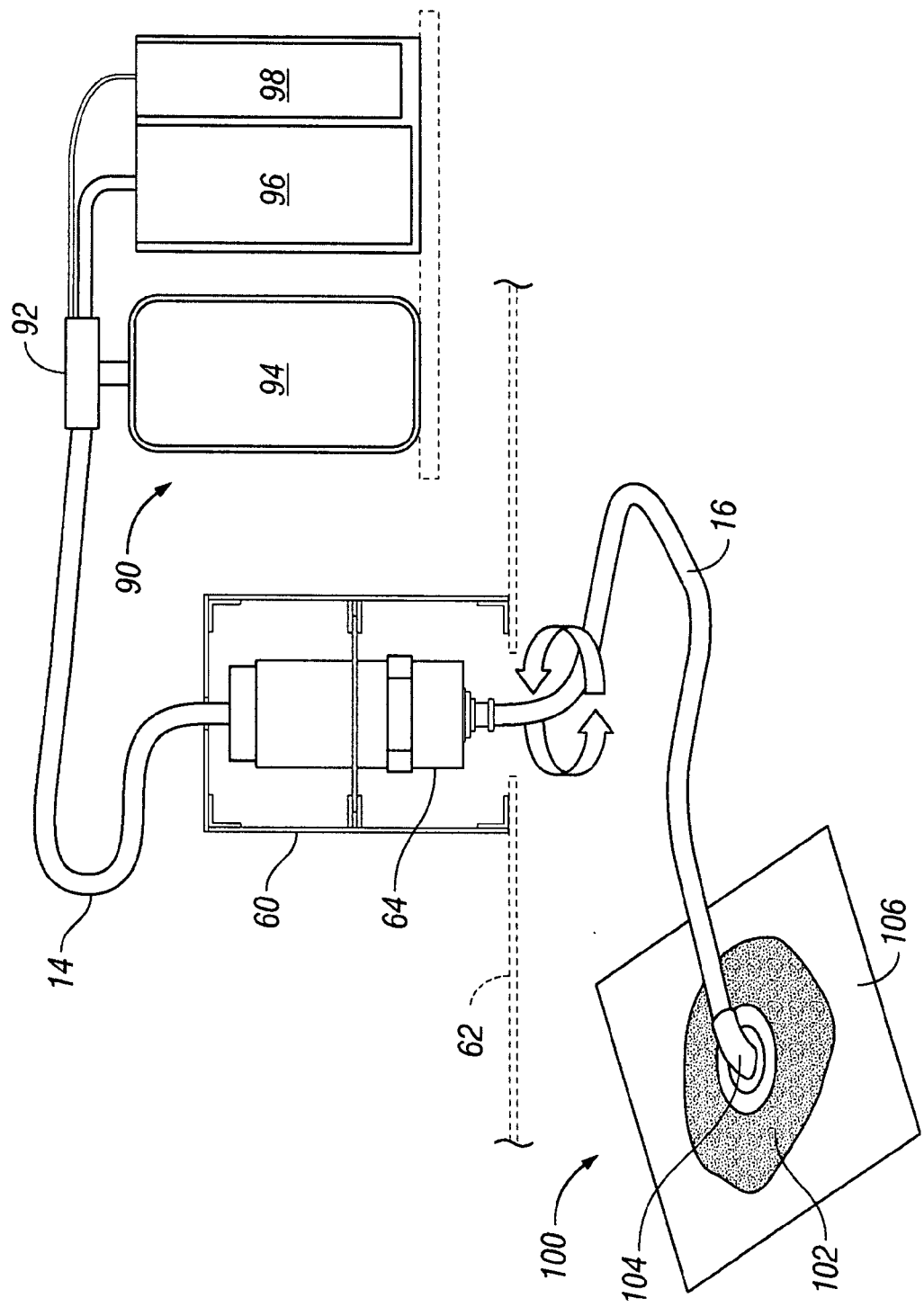
FIG. 6 is a schematic side view, with a portion shown in perspective view, of a reduced pressure treatment system incorporating a swivel connector and bracket assembly according to an embodiment of the present invention.
Figure 7:
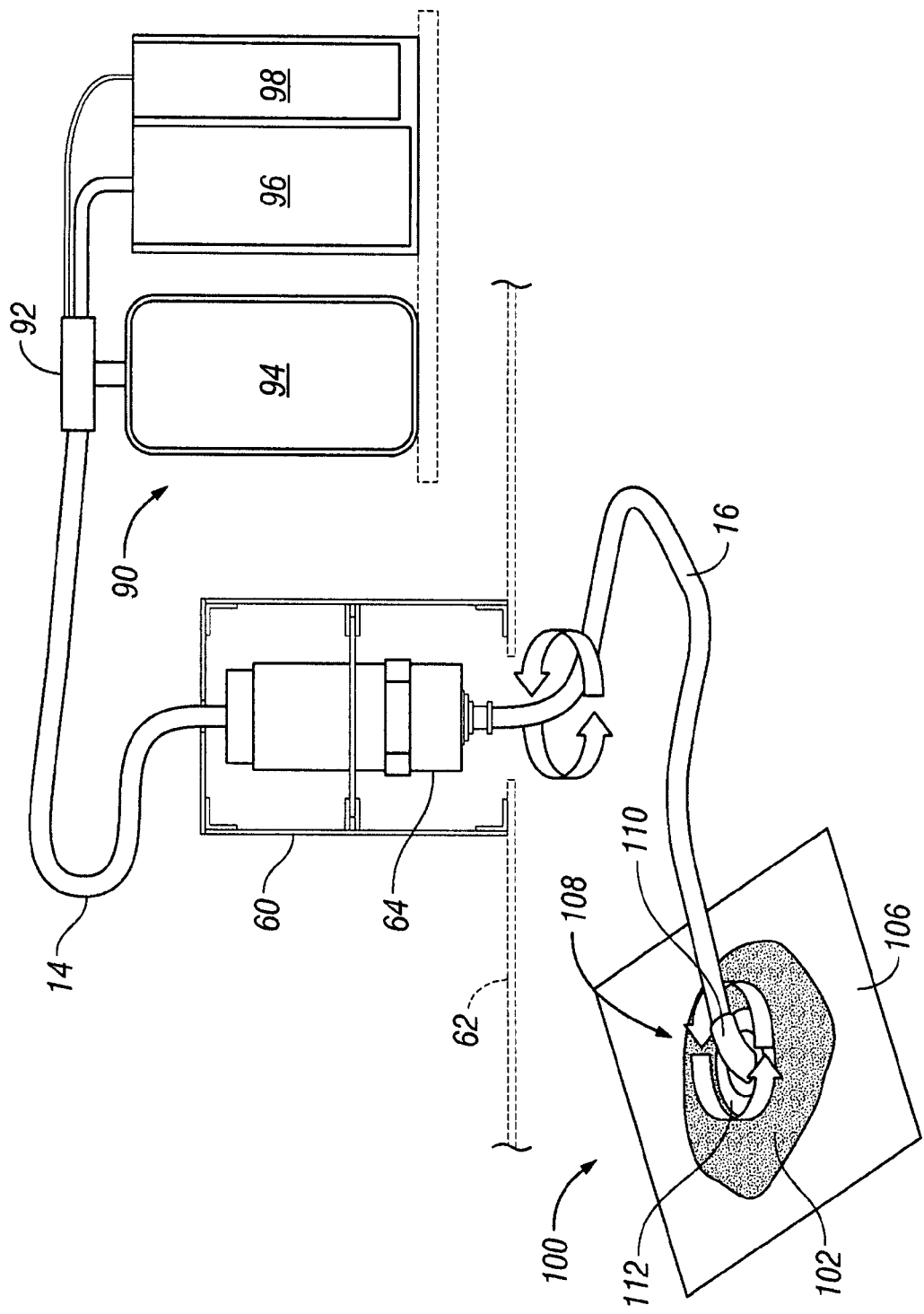
FIG. 7 is a schematic side view, with a portion shown in perspective view, of a reduced pressure treatment system incorporating a swivel connector and a rotating adapter at a dressing according to an embodiment of the present invention.

Referring to FIG. 1, a swivel connector assembly 5 according to an embodiment of the present invention includes stationary components 10 and rotational components 12. In FIG. 1, a section of multi-lumen conduit 14 is connected between the swivel connector assembly 5 and the reduced pressure treatment system instrumentation (as shown in FIGS. 6 and 7). A second conduit 16 extends from the swivel connector assembly 5 to a subject animal or patient, or more specifically, to a dressing positioned on the subject. In general, an axial line indicated in dashed and dotted format in FIG. 1 represents the axis of assembly and symmetry around which these generally cylindrical components are placed and connected.

The stationary components 10 may include a bulkhead 18, which receives the conduit 14 through a central passage 19. The bulkhead 18 is positioned within and is rigidly connected to a connection collar 20, which is generally stationary with respect to the reduced pressure treatment system instrumentation and which forms a first half of two threaded enclosure components. In certain embodiments, the connection collar 20 may be a PVC component of the type typically used to connect a PVC pipe section to a female (threaded) iron pipe (FIP) section. The connection collar 20 includes a threaded section that allows adjustability of the swivel connector. The threaded section is preferably internal to the connection collar 20.

The stationary components 10 may further include a conduit adapter 22, which is attached to conduit 14 only after conduit 14 has passed through the central passage 19 of the bulkhead 18. The conduit 14 typically is press-fit into the conduit adapter 22. A set screw 23 or other fastener may secure the conduit adapter 22 within the central passage 19 of the bulkhead 18. Likewise, a plurality of set screws (3 or 4 in certain embodiments) may secure the bulkhead 18 within the connection collar 20, one of which is seen in the orientation of FIG. 1. Alternatively, either the central passage 19 or the conduit adapter 22 may be tapered so that conduit adapter 22 is rigidly fixed in the bulkhead 18 when pressed into position.

Forming the second half of the two threaded enclosure components, connectable to the connection collar 20, is a bearing collar 26. In one embodiment, the bearing collar 26 is constructed in the manner of a PVC adapter of the type that connects a PVC pipe to a male (threaded) iron pipe (MIP) fitting. A spacer collar 24 may be positioned around the threads of bearing collar 26 in order to control the tightness of the connection and the seal between the internal conduit adapter 22 and a conduit collar 30. Also among the stationary components 10 is a snap ring 28, which may be compressed inward and then released to fit within a slot 29 positioned in the bearing collar 26 once the rotational components 12 (described in detail below) have been installed therein. Also shown in conjunction with the stationary components 10 is a mounting plate 36, positioned between the connection collar 20 and the bearing collar 26. A large central aperture receives the threaded section of the bearing collar 26 and permits the threaded rotation of the bearing collar 26 into or out of the connection collar 20, as described. The mounting plate 36 may include a plurality of peripheral bolt holes to attach the plate, and thus the swivel connector assembly 5, to a bracket or the like associated with an animal enclosure. Typically, the mounting of the swivel connector assembly 5 would be in a position above an animal on the top of an enclosure or on a bracket extending from the top edge of a wall of the enclosure.

The conduit adapter 22 is secured within the combination of the stationary components 10 and attached to the conduit 14 through the bulkhead 18. The geometry of the conduit adapter 22 and the conduit collar 30 are coaxially aligned within the enclosure components when the enclosure components are fixed in place, as described. The tightness with which the conduit adapter 22 and the conduit collar 30 are mated is controlled in part by the degree to which the bearing collar 26 is threaded into the connection collar 20. The connection collar 20, the bearing collar 26, and the spacer collar 24 are preferably constructed of PVC material. The bulkhead 18 is preferably constructed from a cylindrical block of polyoxymethylene plastic sold under the trademark DELRIN.

The rotational components 12 may include the conduit collar 30, a first shaft member 32, and a portion of a bearing assembly 34. The bearing assembly 34 may include one or more bearing sets 35 (two shown in FIG. 1). Each bearing set 35 generally includes an inner race (not shown) and an outer race 39, separated by ball bearings, roller bearings, or other beatings. The inner race of each bearing set 35 is positioned on a second shaft member 37, which includes a flanged end 38. The multi-lumen conduit 16 passes through the second shaft member 37 and the first shaft member 32 to a point where it press-fits into the conduit collar 30. This combination of the multi-lumen conduit 16 and the conduit collar 30 is positioned within a central bore 33 of the first shaft member 32, and may be fixed there with a set screw 23 or other fastener through a drilled aperture in shaft 32, as shown. The first shaft member 32 is positioned onto the second shaft member 37, and likewise may be rigidly fixed thereto with a set screw 23 or other fastener through the drilled aperture in shaft 32. Alternatively, the second shaft member 37 may be extended and manufactured to include the central bore 33, such that a separate first shaft member 32 is not necessary. If the first shaft member 32 and the second shaft 37 member are manufactured as separate components, the first shaft member 32 is preferably constructed from a cylindrical block of polyoxymethylene plastic sold under the trademark DELRIN, and is generally of sufficient length to extend through the bearing collar 26 so that conduit collar 30 may be inserted into conduit adapter 22 when the components are assembled.

The bearing assembly 34 provides a heavy duty, rotatable assembly that receives the multi-lumen conduit 16. As mentioned above, the axial alignment and assembly of the entire set of components (both stationary and rotating) is generally indicated by the axial line shown in FIG. 1. The snap ring 28 is withdrawn from this linear arrangement of components until such time as the assembly of rotating components 12 is inserted into the stationary components 10, whereafter the snap ring 28 is put into place and serves to hold the entire assembly of rotating components 12, and in particular the bearing assembly 34, within the enclosure established by the stationary components 10. As additional protection for the multi-lumen conduit 16, a flexible metal sheath (not shown), such as of a BX Cable type, may encapsulate the conduit 16 and be attached to the flanged end 38 of the shaft 37. The flexible sheath extends from the swivel connector to a dressing (or harness) positioned on a subject animal or patient. Such a sheath rotates with the conduit 16 and the rotational components 12. The sheath protects the conduit 16 from being damaged by chewing or other activity by the animal or patient, and also transmits rotational force from the dressing to the swivel connector 5.

The conduit adapter 22 and the conduit collar 30 mate together loosely in a manner described in more detail below, but are held in position against each other by the structural geometry of the components and the enclosure shown. The degree of insertion of the conduit collar 30 into the conduit adapter 22 determines the tightness of the seal between the conduit 14 and the conduit 16. An o-ring 42 within the conduit adapter 22 mates with an end surface 45 of the conduit collar 30 when the conduit collar 30 is inserted within the conduit adapter 22. The amount of force exerted by the conduit collar 30 on the o-ring 42 determines the ease with which the conduit collar 30 rotates within the conduit adapter 22. This force may be increased by tightening the threaded connection between the bearing collar 26 and the connection collar 20. Similarly, the force applied by the conduit collar 30 to the o-ring 42 may be decreased by loosening the threaded connection between the bearing collar 26 and the connection collar 20.

The bearing assembly 34 permits the rotational components 12 to rotate freely but for the frictional contact between the o-ring 42 and the conduit collar 30. Turning the bearing collar 26 with respect to the connection collar 20 to tighten the swivel connector assembly 5 increases the friction between the o-ring 42 and the conduit collar 30, and thereby reduces the ease with which the swivel connector assembly 5 turns. Conversely, turning the bearing collar 26 to loosen the swivel connector assembly increases the ease with which the swivel connector assembly 5 turns. While it is desired that the rotational components 12 rotate easily within the stationary components 10, the conduit collar 30 must engage the o-ring 42 with enough force to maintain a seal between the conduit collar 30 and the conduit adapter 22. To lessen the frictional force between the conduit collar 30 and the o-ring 42, a lubricant is preferably applied to the o-ring 42.

Figure 2A:
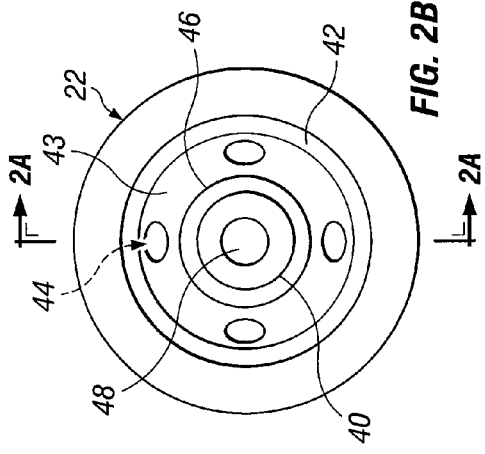
FIG. 2A is a schematic cross-sectional view of a conduit adapter of the swivel connector assembly of FIG. 1.

The internal structure of the conduit adapter 22 and the conduit collar 30, shown in greater detail in FIGS. 2A, 2B, 3A, and 3B, allow fluid communication between ancillary lumens in the multi-lumen conduits 14 and 16 without interruption and without cross contamination with the primary lumen. As shown in FIG. 2A, the conduit adapter 22 includes a bayonet connector 40 having a bore 48, a housing 41, and a support member 43. The support member 43 provides a generally rigid connection between the housing 41 and the bayonet connector 40. One or more apertures 44 penetrate the support member 43. In the embodiment illustrated in FIG. 2A, the support member 43 has a width that is thin relative to the length of the bayonet connector 40 and the housing 41. Alternatively, though, the support member 43 may have any configuration that maintains the position of the bayonet connector relative to the housing 41 while permitting fluid communication through the support member 43. The bayonet connector 40 penetrates and engages the primary lumens of the conduit 14 and the conduit 16. A conduit stop 46 limits the penetration of the bayonet connector 40 into the conduit 14 so as to maintain a cavity between the conduit 14 and the aperture 44. The conduit stop 46 also may limit the penetration of the bayonet connector 40 into the conduit 16. Alternatively, the bayonet connector 40 may be tapered to limit the penetration into the conduit 14 and the conduit 16. The bayonet connector 40, the housing 41, and the support member 43 may be manufactured as a single integrated component, or as separate components that are subsequently assembled. The o-ring 42 is positioned to provide an appropriate seal to isolate the ancillary lumens of the conduit 16 from the external environment when the conduit adapter 22 and the conduit collar 30 are assembled. A second o-ring (not shown) may optionally be positioned in the interior of the conduit adapter 22 on the side of the support member 43 opposite the o-ring 42 to further seal the ancillary lumens of the conduit 14 from the external environment.

Figure 2B:
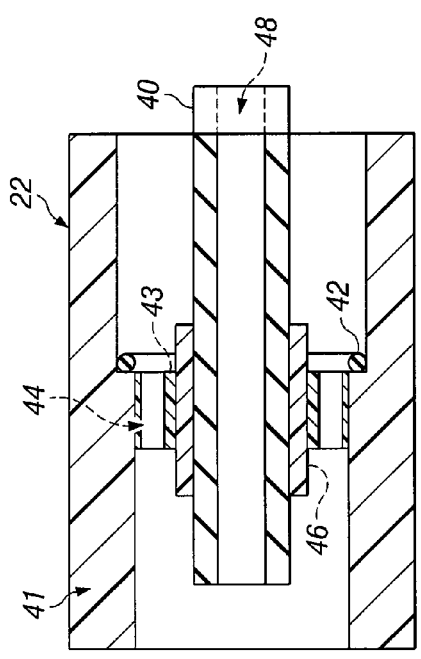
FIG. 2B is a schematic end view of the conduit adapter of FIG. 1.

FIG. 2B illustrates one embodiment of the peripheral apertures 44 in the conduit adapter 22 that permit fluid communication between the ancillary lumens of the multi-lumen conduits 14 and 16.

Figure 3A:
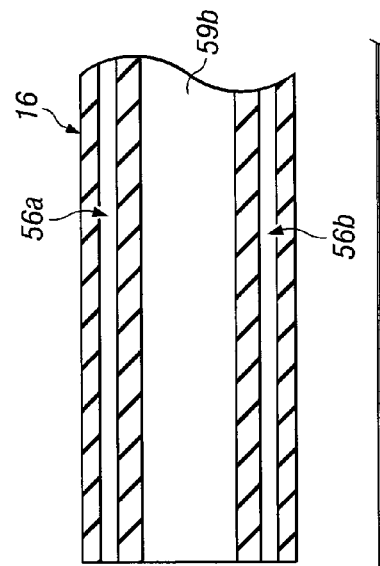
FIG. 3A is a schematic, longitudinal cross-sectional view of a conduit collar.
Figure 3A:
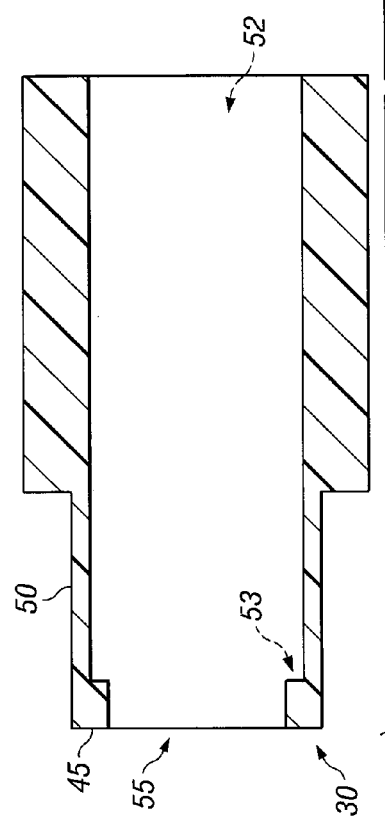

A cross-section of the conduit collar 30 is shown in FIG. 3A, aligned with the multi-lumen conduit 16. An external surface 50 of the conduit collar 30 is sufficiently smooth to allow the conduit collar 30 to rotate within the conduit adapter 22. The internal bore 52 of the conduit collar 30 is sized to accommodate the press-fit insertion of the conduit 16, which generally includes a primary lumen 59b and ancillary lumens 56a and 56b. A conduit stop 53 limits the penetration of the conduit 16 into the conduit collar 30, leaving a gap between opening 55 and the end of the conduit 16. It should be noted that some variation in the depth with which the conduit collar 30 may be inserted into the conduit adapter 22 allows for similar variations in the tightness of the overall swivel connection.

Figure 3B:
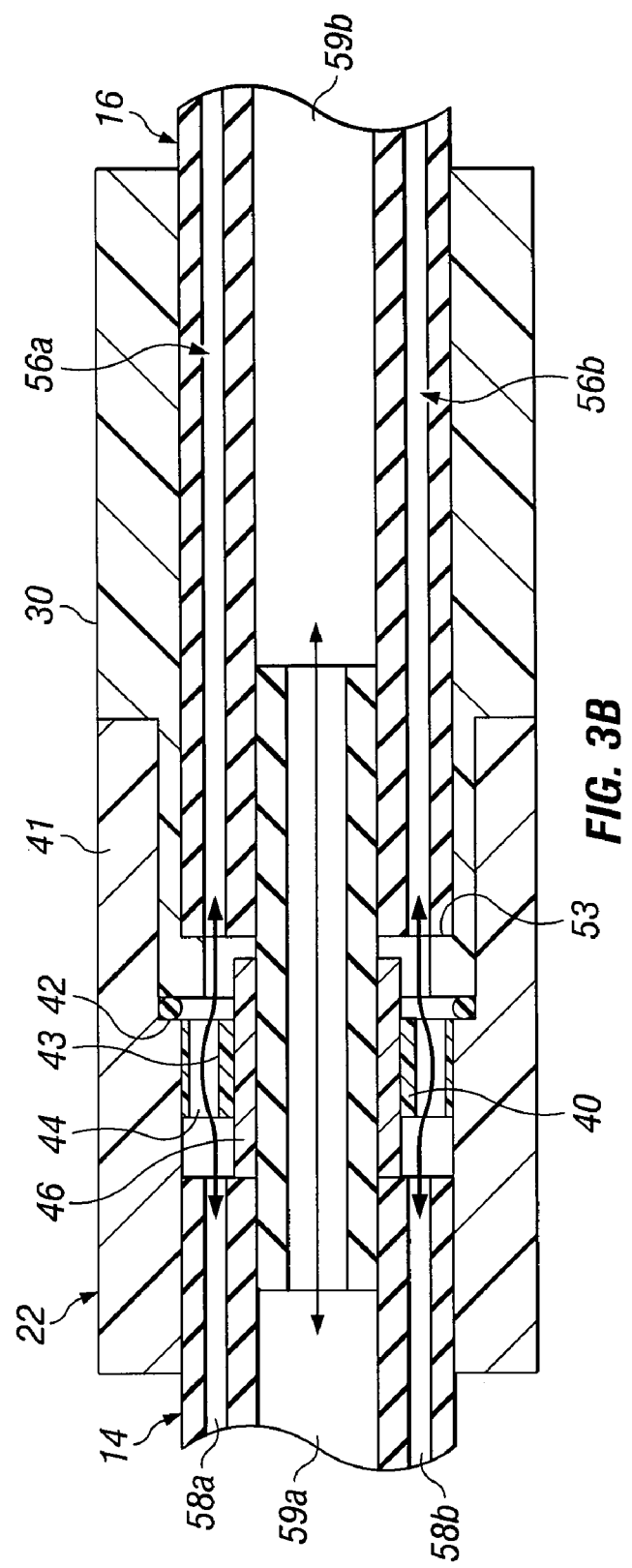
FIG. 3B is a schematic, cross-sectional side view of the conduit collar of FIGS. 1 and 3A and a second multi-lumen conduit inserted into the conduit adapter of FIGS. 1 and 2A having a first multi-lumen conduit.

FIG. 3B is a cross-section of an assembly comprising the conduit 14, the conduit adapter 22, the conduit collar 30, and the conduit 16. The conduit 14 is pressed into position in the conduit adapter 22 so that the primary lumen 59a engages the bayonet connector 40. The conduit 16 is pressed into the conduit collar 30, which is pressed into the end of the conduit adapter 22 so that the primary lumen 59b engages the bayonet connector 40 on the end opposite the conduit 14. Moreover, the conduit stop 46 (or the taper of bayonet connector 40) prevents the conduit 14 from contacting the support member 43. Consequently, there is a cavity between the ancillary lumens 58a and 58b and the apertures 44 in the support member 43. Likewise, the conduit collar 30 prevents the conduit 16 from contacting the support member 44, leaving a cavity between the ancillary lumens 56a and 56b and the apertures 44. The cavity on each side of the apertures 44 permits fluid communication between the ancillary lumens via the apertures 44, regardless of the relative orientation of the conduits 14 and 16.

Figure 4:
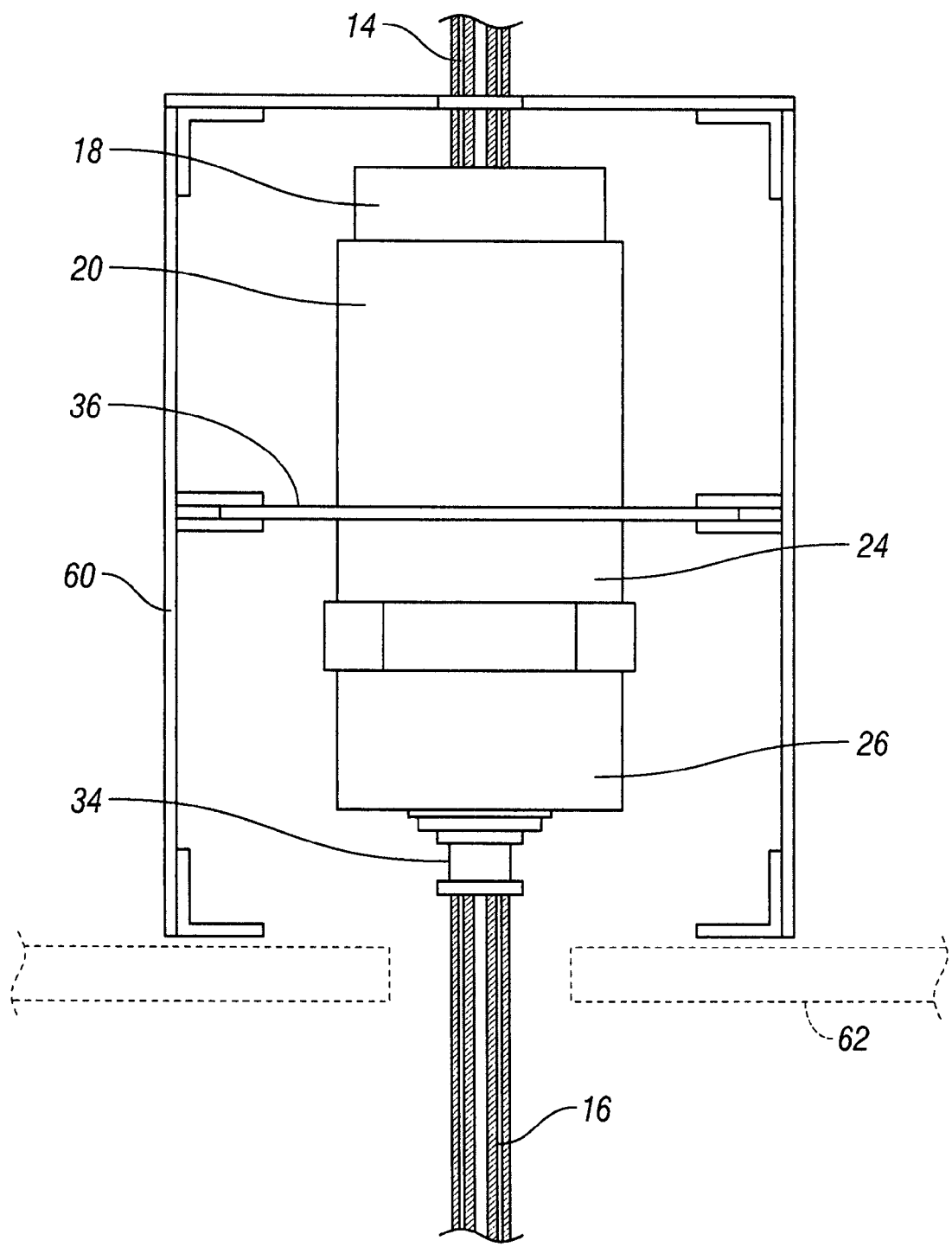
FIG. 4 is a schematic side view of the assembled swivel connector assembly of FIG. 1 positioned on a bracket assembly with the multi-lumen conduits shown in cross section.

FIG. 4 provides an example of the manner in which a swivel connector assembly may be mounted over or on top of an enclosure or the like. A bracket frame 60 receives and retains a mounting bracket 36 as shown. The frame 60 provides a variety of mounting apertures to position and secure the frame and the swivel connector to some part of the enclosure 62.

Figure 5:
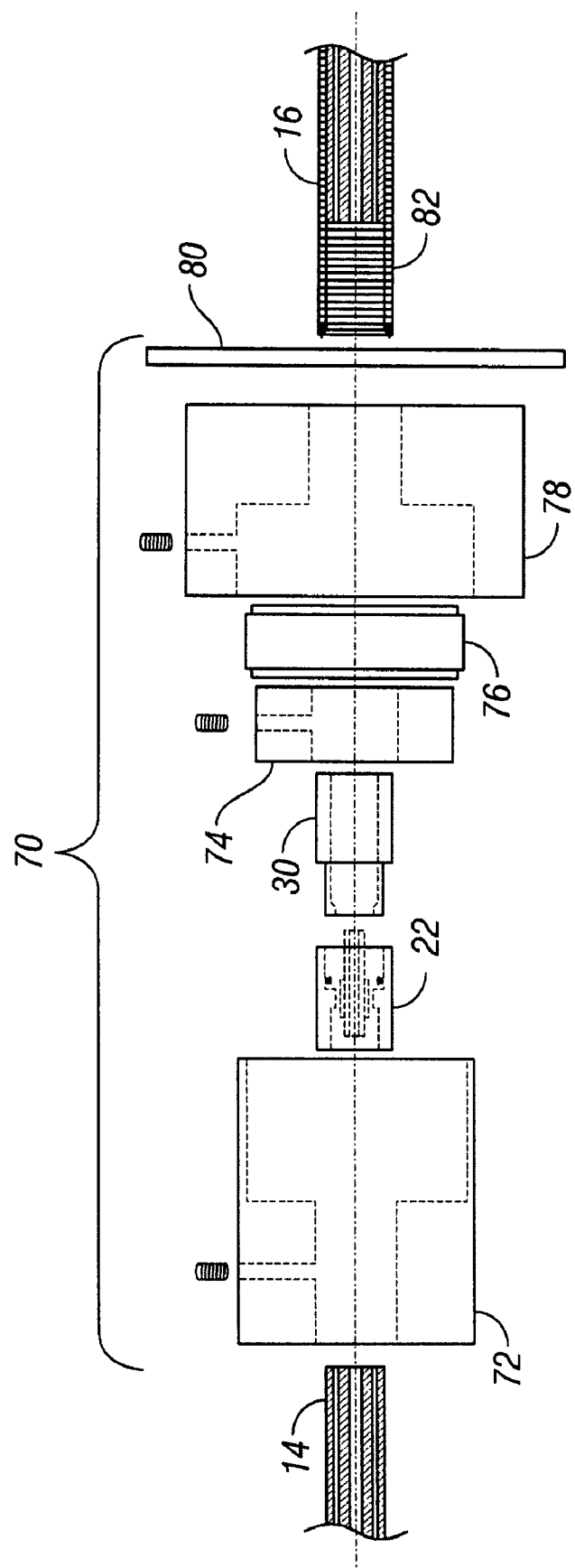
FIG. 5 is a schematic, exploded side view, with a portion shown with broken lines, of a swivel connector assembly according to another embodiment of the present invention, the swivel connector assembly is shown with multi-lumen conduits in cross section.

Reference is finally made to FIG. 5 for a brief description of an alternate embodiment of the invention, sized and dimensioned to be suitable for use in conjunction with smaller animal subjects. The basic principles of the previously described embodiment are retained in the assembly 70 shown in FIG. 5 with commensurate reductions in size and weight to a number of the components.

The conduit adapter 22 and the conduit collar 30 of the connector assembly are the same as in the previous description, as are the conduits 14 and 16. Wire wound conduit shield 82 is provided in this embodiment to cover the length of the conduit 16 that extends from the swivel connector to the subject animal. The rotating components of the embodiment shown comprise the conduit 16, the conduit shield 82, the conduit collar 30, the shaft 74, and the bearing assembly 76. The shaft 74 retains the conduit shield 82 by way of a set screw 23 or other fastener, and thereby retains the conduit collar 30 attached to the conduit 16. The shaft 74 and the bearing assembly 76 may be a unitary component or separate components. The bearing assembly 76 is secured (by way of the stationary exterior portion of the bearing) within the bearing collar 78.

The stationary components of this alternative embodiment include the bearing collar 78, the bulkhead 72, the conduit adapter 22, and the conduit 14. As in the previously described embodiment, the conduit adapter 22 is press-fit onto the conduit 14 after the conduit 14 has passed through a central bore in the bulkhead 72. These two components are then secured within bulkhead 72 by way of a set screw 23 or other fastener, as shown. A mounting bracket 80 is independently attached to the bearing collar 78, rather than included in the threaded assembly described above. This may be accomplished by either attaching the bracket 80 to the bearing collar 78 by way of screws or bolts or by clamping the bearing collar 78 within a mounting frame (not shown) that is itself attached to the mounting bracket 80. The bracket 80 has a central aperture to permit the passage of the combination of the conduit shield 82 and the conduit 16.

Operation of the embodiment shown in FIG. 5 is similar to that described above. The components shown serve to position the conduit adapter 22 and the conduit collar 30 such that upon assembly of the swivel connector they align and engage to complete the conduit connection. The use of the described embodiment only in conjunction with a smaller sized animal subject reduces the need for variation in the tightness of the seal and therefore of the rotational freedom of the swivel. Some variation may be achieved by varying the specific placement of the set screws involved in the assembly of the device, but is not generally required in practice. As with the first described embodiment, the swivel may be mounted to an enclosure (not shown) or the like, preferably in a vertical orientation with the combination of the conduit shield 82 and the conduit 16 being directed to an animal subject from above.

FIG. 6 illustrates a swivel connector in conjunction with a reduced pressure treatment system. The swivel connector 64 is positioned within a bracket frame 60, which is in turn secured to an elevated support structure 62 as described above. The conduit 14 connects to the reduced pressure treatment system instrumentation 90, which comprises an effluent collection container 94, a reduced pressure pump 96, and monitoring instrumentation 98. These instrumentation components are connected to the conduit 14 by way of a manifold connector 92 in a manner known in the art. The combination of the reduced pressure treatment instrumentation 90 and the swivel connector assembly comprise the stationary components of the overall reduced pressure treatment system.

The movable components of the reduced pressure treatment system begin at the swivel connector 64 and extend towards an animal subject or human patient by way of the conduit 16. The conduit 16 connects to the tissue treatment site, typically through a dressing 100 as shown. In FIG. 6, the dressing 100 comprises a granulated foam material 102 positioned within the tissue, with an adapter 104 positioned in a centralized location on the foam material 102. An adhesive drape 106 is typically placed over the foam 102, but allows for passage through to the adapter 104. The conduit 16 connects the dressing 100 to the swivel connector 64 in a manner that permits the generally free movement (rotation) of the conduit 16 below the swivel connector. In the case of animal subjects it may be necessary to position the dressing 100 within a harness that immobilizes the conduit 16 on the animal subject and transfers the required motion up to the swivel connector 64. Similar, although typically less substantial, patient conduit immobilizing measures may be taken with human subjects as well, in order to direct the rotational motion up to the swivel connector 64, which is designed to accommodate such motion. In this manner, the system of the present invention allows for the maintenance of the integrity of the conduit connecting the reduced pressure treatment instrumentation 90 with the tissue treatment site while permitting greater freedom of motion for the animal subject or human patient.

FIG. 7 discloses an alternate arrangement of the system shown generally in FIG. 6 with the substitution of a rotating adapter 108 coupled to the dressing 100. The components the adapter 108 may be configured to allow the rotation of the port connection 110 with respect to the dressing 100 as shown. In this manner, some of the required motion (rotation) may be accommodated by the adapter 108, and some of the motion transferred to the swivel connector 64. The result is even greater freedom of motion with less force required given the additional location of rotational movement.

Figure 8:
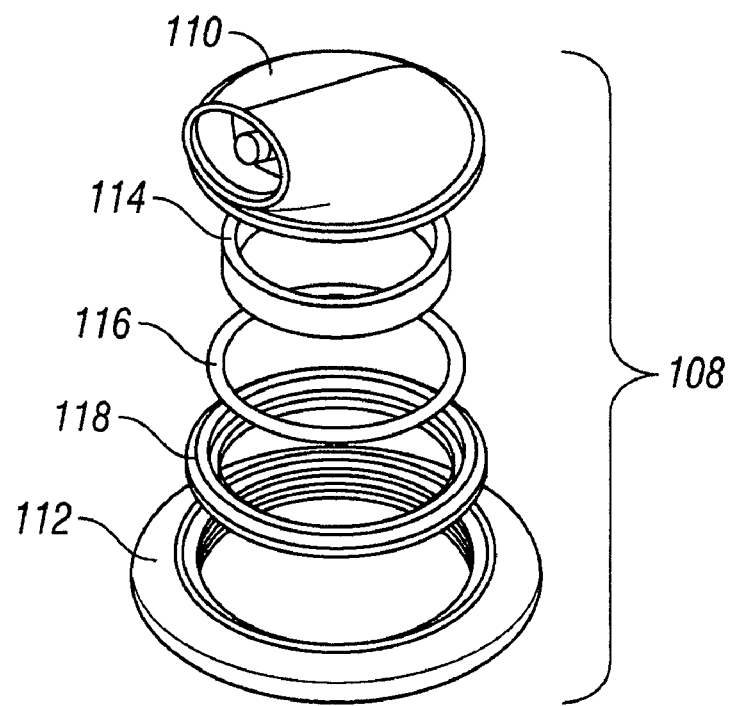
FIG. 8 is an exploded perspective view of the rotating adapter of FIG. 7.
Figure 9:
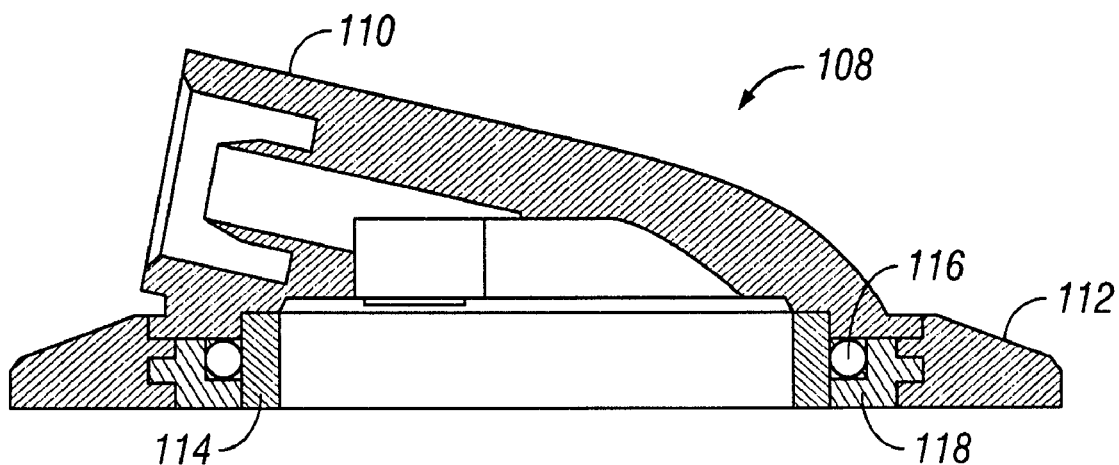
FIG. 9 is an assembled cross-sectional side view of the rotating adapter of FIG. 8.

Reference is finally made to FIGS. 8 and 9 for a description of the configuration of the rotating adapter 108 shown in FIG. 7. The rotating adapter 108 shown in FIG. 8 employs a hard plastic inner core that forms a bearing surface to enable a rubber o-ring to seal against it and also to enable the bearing surface to slide past with relatively low friction. Bonded to the hard plastic inner core is a soft thermoplastic or elastomeric polymer that acts as a protective and cushioning cover. FIGS. 8 and 9 show the various circular ring components that go together to make up the rotating adapter 108. A top rotating PVC component 110 covers a top ABS insert ring 114, which is surrounded by a rubber o-ring 116. A bottom ABS insert ring 118 is shown that holds o-ring 116 captive between it and the top ABS insert 114. Each of these rings is then fitted within the bottom PVC ring 112, which contacts with the dressing 100.

FIG. 9 discloses the same components of the rotating adapter 108 described above as they would be assembled and thereby shows in clearer detail the manner in which the components interlock and rotate with or against each other. In this view, the captive o-ring 116 is also shown to provide a proper seal for the internal reduced pressure chamber formed by the rotating adapter 108. In this view it is also clear how the internal features and elements in the port opening are configured to appropriately position the reduced pressure treatment conduits at the dressing 100 regardless of the rotational orientation of the conduit connected to the adapter 108.

Once again, however, in either of the embodiments shown in FIGS. 6 & 7, the system allows for the maintenance of the integrity of the conduit connecting the reduced pressure treatment instrumentation 90 with the tissue site while permitting greater freedom of motion for an animal subject or human patient.

Although the invention has been described in terms of the foregoing preferred embodiments, this description has been provided by way of explanation only, and is not intended to be construed as a limitation of the invention. Those skilled in the art will recognize modifications that might accommodate specific animal subjects, human patients, and tissue healing environments. Such modifications as to size, geometry, and even system configuration, where such modifications are merely coincidental to the animal subject, the human patient, to the type of tissue, or to the type of treatment being applied, do not necessarily depart from the spirit and scope of the invention.

We claim:

1. An apparatus for connecting multi-lumen conduits, each multi-lumen conduit having a primary lumen and at least one ancillary lumen, the apparatus comprising:
    a conduit adapter having:
    a housing having a first end and a second end,
    a tubular connector positioned within the housing and having a bore extending along the longitudinal axis of the tubular connector, wherein a first end of the tubular connector is configured to receive a first multi-lumen conduit, and
    a support member connecting the housing and the tubular connector, wherein the support member is formed with at least one aperture therethrough;
    a conduit collar having a first end and a second end and having an internal bore, the first end being sized for insertion into the second end of the housing and rotational within the housing, the second end of the conduit collar being configured to receive a second multi-lumen conduit within the internal bore of the conduit collar;
    wherein the tubular connector is configured to rotationally engage the primary lumen of the second multi-lumen conduit while permitting fluid communication between the primary lumens of the first end and second multi-lumen conduits via the bore of the tubular connector;
    wherein the support member is configured to permit fluid communication between the at least one ancillary lumen of the first and second multi-lumen conduits via the at least one aperture;
    wherein the bore of the tubular connector is configured to maintain fluid communication between the primary lumens and the at least one aperture maintains fluid communication between the ancillary lumens when the first and second multi-lumen conduits are subjected to relative rotation between them;
    wherein the conduit adapter is secured to a bulkhead;
    a bearing collar rigidly secured to the bulkhead;
    a first shaft member having a first end rigidly secured to the conduit collar, and a second end; and
    a bearing assembly fixed on the second end of the first shaft member and rigidly positioned within the bearing collar whereby the conduit collar and the second multi-lumen conduit are free to rotate within the bearing collar relative to the bulkhead.

* * * * *